(12) United States Patent
Wu et al.

(10) Patent No.: US 8,173,622 B2
(45) Date of Patent: May 8, 2012

(54) ANTIMICROBIAL COMPOUNDS HAVING PROTECTIVE OR THERAPEUTIC LEAVING GROUPS

(75) Inventors: Paul Hsien-Fu Wu, Edina, MN (US); Catherine E. Taylor, Fridley, MN (US); Linnus Cheruiyot, Andover, MN (US); Jianwei Li, Woodbury, MN (US); Terese A. Bartlett, Forest Lake, MN (US); Matt Bergan, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 379 days.

(21) Appl. No.: 12/192,268

(22) Filed: Aug. 15, 2008

(65) Prior Publication Data
US 2009/0047321 A1   Feb. 19, 2009

Related U.S. Application Data

(60) Provisional application No. 60/956,068, filed on Aug. 15, 2007.

(51) Int. Cl.
*A01N 55/00* (2006.01)
(52) U.S. Cl. .............................. 514/63; 528/10
(58) Field of Classification Search .................. None
See application file for complete search history.

(56) References Cited

U.S. PATENT DOCUMENTS

| 4,208,312 | A | * | 6/1980 | Okada et al. ............... 524/773 |
| 4,292,219 | A | | 9/1981 | Lyons et al. |
| 4,565,883 | A | * | 1/1986 | Sieger et al. ............... 549/475 |
| 5,449,734 | A | * | 9/1995 | Kotani et al. ............... 528/12 |
| 2003/0129397 | A1 | * | 7/2003 | Wilson et al. ............... 428/375 |
| 2006/0194764 | A1 | | 8/2006 | Kim et al. |
| 2008/0125728 | A1 | | 5/2008 | Bischoff et al. |

FOREIGN PATENT DOCUMENTS

| JP | 06049220 A | * | 2/1994 |
| JP | 09263731 A | * | 10/1997 |
| JP | 2007-217683 A | | 8/2007 |
| WO | WO 2007/019478 A2 | | 2/2007 |

OTHER PUBLICATIONS

English Machine translation of above JP 06049220A Feb. 1994 (9 pages).*
English Machine translation of above JP 09263731A Oct. 1997 (43 pages).*
(PCT/US2009/053340) PCT Notification of Transmittal of the International Search Report and the Written Opinion of the International Searching Authority.
Database Registry, "Benzoic Acid, 4-(phenylmethoxy)-ethyl ester", Nov. 16, 1984, XP002552306.
Database Registry, Benzene, [1-methyl-1-(2-propen-1-yloxy)ethyl], Nov. 16, 1984, XP002552307.
Database WPI Week 200780, Thomson Scientific, London, GB, AN 2007-864588 & JP 2007 217683A (Hitachi Chem Co Ltd) Aug. 30, 2007, XP002662308.
Yun-mi Kim et al., Structure-Antimicrobial Activity Relationship for Silanols, a New Class of Disinfectants, Compared with Alcohols and Phenols, International Journal of Antimicrobial Agents 29 (2007) 217-222.
Yun-mi Kim et al., Silanol—A Novel Class of Antimicrobial Agent, Electronic Journal of Biotechnology ISSN: 0717-3458, vol. 9, No. 2, Issue of Apr. 15, 2006.

* cited by examiner

*Primary Examiner* — Bethany Barham
(74) *Attorney, Agent, or Firm* — Mueting Raasch & Gebhardt, P.A.

(57) ABSTRACT

Antimicrobial compounds, such as silanol or alcohol, include a protecting or leaving group that can protect the compound from degradation during the process of preparing a medical device containing the compound or reduce the volatility of the compound relative to its counterpart without the leaving group. Nearly any hydrolysable leaving group may be employed. The leaving group may be an agent that may serve a therapeutic function in addition to protecting or retaining the antimicrobial agents.

18 Claims, 1 Drawing Sheet

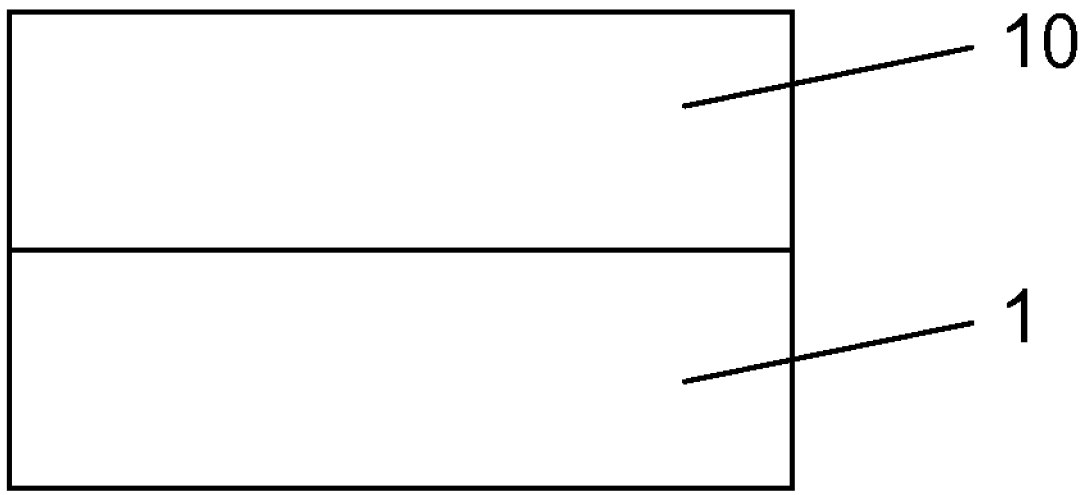

ANTIMICROBIAL COMPOUNDS HAVING PROTECTIVE OR THERAPEUTIC LEAVING GROUPS

RELATED APPLICATION

This application claims the benefit of provisional U.S. Application Ser. No. 60/956,068, filed Aug. 15, 2007.

FIELD OF THE INVENTION

This application relates to antimicrobial agents for medical devices and methods for forming devices having antimicrobial agents; and, more particularly, to compounds, compositions and methods employing antimicrobial alcohols or silanols or compounds hydrolysable into alcohols or silanols.

BACKGROUND OF THE INVENTION

Silanol compounds have been reported to possess antimicrobial activity. The antimicrobial activity may be due to high acidity and hydrophobicity relative to their alcohol counterparts. However, use of silanols as antimicrobial agents in medical device applications has drawbacks. For example, silanols tend to be volatile. Some silanols may also undergo condensation reaction and form siloxanes. Both of these characteristics of silanols tends to leave little initial silanol remaining by the time an implantable medical device containing the silanol is implanted in a patient.

SUMMARY

The present disclosure describes hydroxyl compounds (such as silanol or alcohol) that contain a protecting or leaving group that can protect the hydroxyl compound from degradation during the process of preparing a medical device or reduce the volatility of the compound relative to its counterpart without the leaving group. Nearly any hydrolysable leaving group may be employed. In various embodiments the leaving group is an agent that may serve a therapeutic function in addition to protecting or retaining the silanol.

In an embodiment, a polymeric composition includes a polymeric material and a compound of according to Formula I:

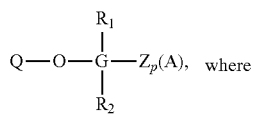

(I)

Q is any hydrolyzable group having a molecular weight greater than or equal to methyl or greater than about 15 Daltons,
$R_1$ and $R_2$ are each independently hydrogen or C1-C5 straight or branched chain alkyl, methyl or ethyl;
A is hydrogen or straight or branched chain C1-C18 alkyl unsubstituted or substituted with halo or hydroxyl;
Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;
p is 0 or 1; and
with the proviso that when p is 0, A is not hydrogen.
G is silicon or carbon.

In an embodiment, a compound having the structure of Formula VI is described:

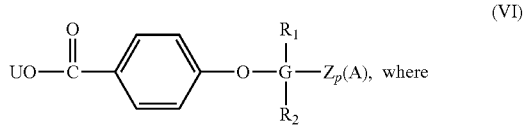

(VI)

U is hydrogen or straight or branched chain C1-C4 alkyl unsubstituted or substituted with halo or hydroxyl;
$R_1$ and $R_2$ are each independently hydrogen or C1-C5 straight or branched chain alkyl;
A is hydrogen or straight or branched chain C1-C18 alkyl unsubstituted or substituted with halo or hydroxyl;
Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;
p is 0 or 1; and
G is silicon or carbon.

A compound according to Formula VI may hydrolyze in situ into an antimicrobial paraben and an antimicrobial silanol, which may provide enhanced antibiotic efficacy relative to the paraben or silanol alone.

In an embodiment, a compound having the structure of Formula I is described:

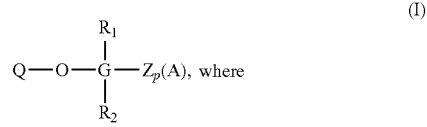

(I)

Q is a precursor to a steroid such that when hydrolyzed to Q-OH, Q-OH acts as a steroid;
$R_1$ and $R_2$ are each independently hydrogen or C1-C5 straight or branched chain alkyl;
A is hydrogen or straight or branched chain C1-C18 alkyl unsubstituted or substituted with halo or hydroxyl;
Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;
p is 0 or 1; and
with the proviso that when p is 0, A is not hydrogen.
G is silicon or carbon.

Such a compound may result in a steroid and an antimicrobial silanol upon hydrolysis in situ.

In an embodiment, a compound having the structure of Formula V is described:

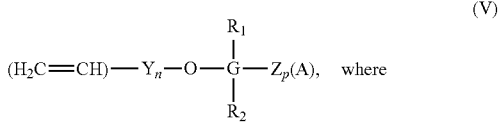

(V)

Y is straight or branched chain C1-C18 alkyl unsubstituted or substituted with halo or hydroxyl;
$R_1$ and $R_2$ are each independently hydrogen or C1-C5 straight or branched chain alkyl;

A is hydrogen or straight or branched chain C1-C18 alkyl unsubstituted or substituted with halo or hydroxyl;

Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;

n, and p are each independently 0 or 1; and

G is silicon or carbon.

Such a compound may be bound to the surface of a device that has been activated by generation of a free radical. The free radical can initiate a bond between the surface of the device and the vinyl group of a compound according to Formula V.

Some of the advantages of the various embodiments described herein will readily understood from the following detailed description when read in conjunction with the accompanying drawings.

BRIEF DESCRIPTION OF THE DRAWINGS

FIG. 1 is a schematic drawing of a cross-section of an implantable medical device and a coating.

The drawing is not necessarily to scale.

DETAILED DESCRIPTION OF THE INVENTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The present disclosure describes, inter alia, silanol compounds that contain a protecting or leaving group that can protect the silanol compound from degradation during the process of preparing a medical device or reduce the volatility of the compound relative to its counterpart without the leaving group. Nearly any hydrolysable leaving group may be employed.

In various embodiments, a polymeric composition includes a polymer material and a compound according to Formula I:

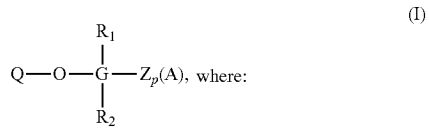

Q is any hydrolysable group having a molecular weight greater than or equal to methyl or greater than about 15 Daltons, $R_1$ and $R_2$ are each independently hydrogen, methyl or ethyl;

A is hydrogen or straight or branched chain C1-C18 alkyl unsubstituted or substituted with halo or hydroxyl;

Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;

p is 0 or 1; and with the proviso that when p is 0, A is not hydrogen.

G is silicon or carbon.

Q may function to decrease volatility of a compound of Formula I relative to its silanol counterpart (i.e., where Q is H). In general the higher the molecular weight of Q, the lower the volatility (or higher the boiling point) of the compound. In various embodiments, Q has a molecular weight greater than about 15 Daltons. For example, Q may have a molecular weight greater than about 50 Daltons, greater than about 100 Daltons or greater than about 200 Daltons. In some embodiments, Q has a molecular weight in the range of between about 15 Daltons and about 10,000 Daltons. For example, Q may have a molecular weight of between about 15 Daltons and about 5,000, or between about 50 Daltons and about 500 Daltons. By decreasing the volatility of the compound of Formula I relative to its silanol counterpart, a higher percentage of the compound can remain in the polymer composition during processing of the composition. This may be particularly desirable in medical device applications in which the polymer composition may undergo extensive processing, including sterilization, prior to being implanted in a patient.

In addition to decreasing volatility or alternatively, Q may be tailored with appropriate functional groups (such as nitro, cyano, halo, amine, hydroxyl, phosphate, perfluoroalkane sulfonate, tosylate, alkyl, aryl alkanes) to adjust the solubility or rate of cleavage of a compound of Formula I relative to its silanol counterpart. Again, with medical devices that can undergo extensive processing prior to being implanted in a patient, decreasing the rate of degradation relative to the silanol may serve to improve efficacy.

Once implanted, Q may be hydrolyzed in situ from a compound of Formula I, yielding Q-OH and a hydroxyl containing compound of Formula II:

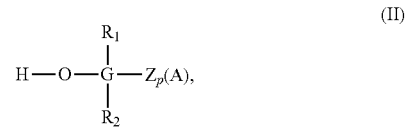

where $R_1$, $R_2$, A, Z, G and p are as described above.

The hydroxyl containing compound according to Formula II, such as a silanol, preferably has antimicrobial activity. Due to its decreased size, relative to a compound of Formula I, a silanol of Formula II may more readily diffuse from the polymeric composition to exert its antimicrobial effect.

As Q is expected to be hydrolyzed following implantation, Q may be selected such that following hydrolysis from a compound of Formula I, Q-OH is a therapeutic agent. In such a manner, Q can serve not only as a protecting or leaving group for the silanol of Formula I, but also provide therapeutic benefit in and of itself. For example, Q-OH may be an antimicrobial agent, an anti-inflammatory agent, an anesthetic, an anti-proliferative agent, anti-hypertension or the like. Q-OH may be a small molecule therapeutic agent or a large molecule agent, such as a polypeptide or polynucleic acid. Nearly any compound having a hydroxyl, carboxylic acid, silanol, silicon-chloride, silicon-anhydride, amine group or the like can be incorporated into a compound according to Formula I according to the teachings presented herein.

Examples of suitable antimicrobial agents that could result from hydrolysis of Q from a compound of Formula I to produce Q-OH include silanols, such as those of Formula II, and antibiotics, such as tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, enoxacin, fleroxacin, temafloxacin, tosufloxacin, clinafloxacin, sulbactam clavulanic acid, amphotericin B, fluconazole, and nystatin.

Other antimicrobial compounds that that could result from hydrolysis of Q from a compound of Formula I to produce Q-OH include antiseptics such as hexachlorophene, para-chloro-meta-xylenol, triclosan, furan medical preparations (i.e. nitrofurantoin, nitrofurazone, silver acetate, silver protein, silver lactate, silver picrate), and alcohols.

Examples of suitable anti-inflammatory agents that could result from hydrolysis of Q from a compound of Formula I to produce Q-OH include steroids, such as dexamethasone, beclamethasone, prednisone, fluticasone hydrocortisone, isoflupredone, methylpredone, triamcinolone acetonide and methyl-prednisilone; and non-steroidal anti-inflammatory agents (NSAIDs), such as salicylates, such as acetylsalicylic acid, amoxiprin, benorylate, benorilate, choline magnesium salicylate, diflunisal, ethenzamide, faislamine, methyl salicylate, magnesium salicylate, salicyl salicylate, salicylamide, and the like; arylalkanoic acids, such as diclofenac, aceclofenac, acemetacin, alclofenac, bromfenac, etodolac, indometacin, oxametacin, sulindac, tolmetin, and the like; 2-arylpropionic acids, such as ibuprofen, alminoprofen, benoxaprofen, carprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen, tiaprofenic acid, and the like; N-arylanthranilic acids, such as flufenamic acid, meclofenamic acid, mefenamic acid, tolfenamic acid, and the like; pyrazolidine derivatives, such as ampyrone, azapropazone, mofebutazone, oxyphenbutazone, and the like; COX-2 inhibitors, such as celecoxib, lumiracoxib, parecoxib, rofecoxib, valdecoxib, and the like; Sulphonanilides, such as nimesulide, and the like; and others, such as licofelone, omega-3 fatty acids, and the like; and the like.

Other anti-inflammatory agents that that could result from hydrolysis of Q from a compound of Formula I to produce Q-OH include antibodies to tumor necrosis factor alpha (TNF-α), soluble receptors to TNF-α, and the like.

Examples of suitable anesthetics agents that could result from hydrolysis of Q from a compound of Formula I to produce Q-OH include local anesthetics agents, such as lidocaine, prilocaine, mepivicaine, bupivicaine and articaine.

Examples of suitable anti-proliferative agents that could result from hydrolysis of Q from a compound of Formula I to produce Q-OH include QP-2 (taxol), actinomycin, methotrexate, vincristine, mitocycin, statins, sirolimus, restenASE, 2-chloro-deoxyadenosine, PCNA (proliferating cell nuclear antigen) ribozyme, batimastat, prolyl hydroxylase inhibitors, halofuginone, C-proteinase inhibitors, probucol, and the like.

Examples of suitable anti-hypertension agents that could result from hydrolysis of Q from a compound of Formula I to produce Q-OH include chlorthalidone, alpha-methyldopa, atenolol, enalapril, amlodipine, and the like. In addition, agents for treating congestive heart failure, such as digoxin, digitoxin, lanatoside C, amrinone, milrinone, remodulin and the like, may be employed to form a compound according to formula I as a therapeutic leaving group.

In numerous embodiments, Q-OH is a small molecule therapeutic agent having a molecular weight less than about 500 Daltons.

In various embodiments, Q of Formula I is alkyl, alkylcarbonyl, alkylamino, halo, tosylyl, or perfluoroalkane sulfonates. Such alkyl groups may include internal amide, keto, ether, isocyanate, or amino groups, or the like. In some embodiments, Q is selected from the group consisting of: (i) a straight or branched chain C1-C18 alkyl unsubstituted or substituted with halo or hydroxy; (ii) $R_4R_5N$—; (iii) an alkali metal;

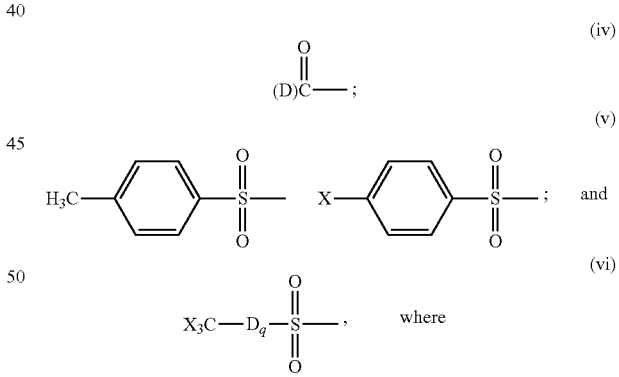

$R_4$ and $R_5$ are each independently hydrogen, methyl or ethyl;
X is halo;
D is straight or branched chain C1-C18 alkyl unsubstituted or substituted with halo or hydroxyl; and
q is 0 or 1.

By way of example, Q may be C1-C3 unsubstituted alkyl, C4-C6 unsubstituted alkyl, C7-C12 unsubstituted alkyl, or C13-C16 unsubstituted alkyl. In various embodiments, X is fluoro. In some embodiments, D and E are be C1-C3 unsubstituted alkyl, C4-C6 unsubstituted alkyl, C7-C12 unsubstituted alkyl, or C13-C16 unsubstituted alkyl. In numerous embodiments, Q is sodium.

With regard to compounds of Formulas I and II above, A in various embodiments is C1-C3 unsubstituted alkyl, C4-C6 unsubstituted alkyl, C7-C12 unsubstituted alkyl, or C13-C16 unsubstituted alkyl. In numerous embodiments, Z is benzene unsubstituted or substituted with an unsubstituted straight chain C1-C3 alkyl.

In some embodiments, a silanol according to Formula II is selected from the group consisting of benzydiethylsilanol, n-butyldimethylsilanol, vinylphenylmethylsilanol, n-propyldimethylsilanol, phenyldimethylsilanol, 3,3,3-trifluoropropyldimethylsilanol, vinyldimethylsilanol, trimethylsilanol, triethylsilanol, t-butyldimethylsilanol, diphenylsilanol, triisopropylsilanol, (p-methoxyphenyl)dimethylsilanol, n-butyldimethylsilanol, (E)-heptenyldiisopropylsilanol, dimethyl (thien-2-yl)silanol, (5,6-dihydro-4H-pyran-2-yl) dimethylsilanol. An alcohol according to Formula II is selected from the group consisting of 2-methy-2-pentanol, 2-methyl-2-hexanol, 2-phenyl-2-propanol, 2-methyl-1-phenyl-2-propanol, and α,α-dimethylbenzene propanol.

Compounds according to Formula I may be made in any suitable manner. In many embodiments, compounds of Formula Ia where G is Si, are formed by reacting a compound of Formula IIa with Q-M as follows:

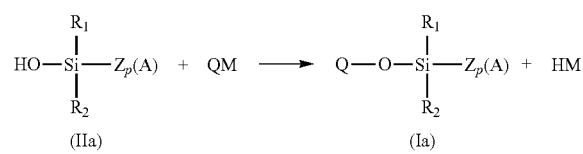

(IIa)   (Ia)

M may be any group capable of undergoing such as reaction. For example, M may be alkoxyl, carboxylic acid, acid chloride, acid anhydride, cyano, amino, tosylyl, perfluoroalkane sulfonate, phosphate, hydroxy, or halo. If Q-OH is a therapeutic agent, it may be convenient for M to be OH, particularly if Q-OH is commercially available.

By way of example, an ester silicone (SiOC) may be prepared by reacting a silanol of Formula IIa with hydroxyl containing chemicals (M=OH) at appropriate temperatures with appropriate solvent(s), such as THF, ethanol, ether, methylene chloride, and an appropriate catalyst if desired. See, e.g., Silicon esters by Barry Arkles, Kirk-Othmer Encyclopedia of Chemical Technology, 4$^{th}$ ed., vol. 22, pp. 69-81.

Of course, any suitable reaction scheme may be employed to produce compounds according to Formulas I and Ia. Due to the relative instability or volatility of silanols, compounds of Formula Ia may be desirably formed by reacting a compound of Formula IIIa with QOM as follows:

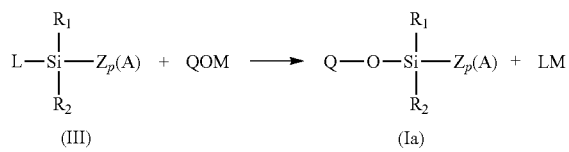

(III)   (Ia)

M may be as described above. L may be any group capable of undergoing such as reaction. For example, L may be halo, hydride, tosylyl, or perfluoroalkane sulfonates.

By way of example, an acetoxy silane (SiOOC) may be prepared by mixing an alcohol with an acetic anhydride and an appropriate catalyst, such as zinc chloride, and heating at an appropriate temperature, e.g., about 75° C. to about 100° C., for an appropriate time, e.g. overnight. By way of further example, a silanol of Formula IIa may be converted to a perfluoro-sulfonate derivative. Alcohol may then be added to react in appropriate solvent, such as THF, at appropriate temperature and time, e.g., about 20 C to about 50 C for about 2 h to about 24 h, to yield compounds with the structure of Formula Ia. See, e.g., Advances in Silicon Chemistry by Gerald L. Larson, Volume 1, pp. 189-301, 1991, JAI Press. In addition, conventional reactions to yield amides may be used in producing compounds with Formula I. This will enable reaction between a compound of Formula II and acid chloride functional group and QM (where M=NH2) to form a compound according to Formula I.

One specific example of a reaction scheme for forming a compound according to Formula Ia is described in Silicon-mediated Transformation of functional Groups by Helmut Vorbruggen (Wiley-VCH), as follows:

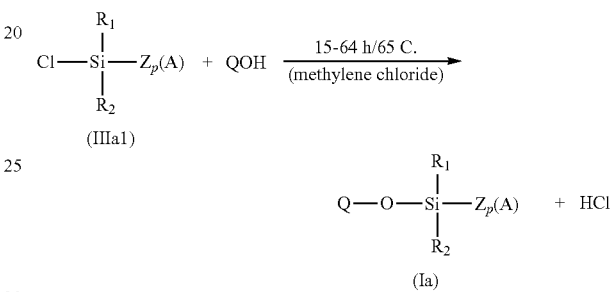

Chemical processes such as solvent extraction, chromatography, decantation, distillation, electrophoresis, evaporation, sieving, precipitation, re-crystallization, centrifuge and filtration may be used for separation or purification during various synthesis steps. Vacuum drying, freeze drying, supercritical drying, spray drying etc. may be used to remove solvent and low volatile intermediates for end product in solid form.

Compounds according to Formula IIa or IIIa may be made in any suitable manner or may be purchased from a variety of vendors, such as Sigma-Aldrich, Inc. or Gelest, Inc. In various embodiments, compounds according to Formula IIa or IIIa are formed from a silane precursor. Any known or future developed reaction conditions may be employed to carryout such a reaction. For example, suitable conditions include those described by E. Choi, et al., Org. Lett., 2002, 4, 2369-2371; and Y. Lee, et al., J. Org. Chem., 2004, 69, 209-212. For example, a silane may be converted to a silanol in the presence of water, an appropriate catalyst, such as ruthenium or iridium catalyst, and solvent, such as Acetonitrile or tetrahydrofuran (THF). Such reactions may take place at room temperature or heated for an appropriate time, such as 10 minutes (min) to 24 hours (h).

While much of the discussion above is with regard to Si compounds and chemistry, it will be understood that much of the same discussion applies to carbon compounds and chemistry.

A polymeric composition including a compound according to Formula I and polymeric material may include any polymeric material. Preferably, the polymeric material is suitable for implanting in a human. Examples of common polymeric materials that may be included in a polymeric composition as described herein include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE). Synthetic or natural bioabsorbable polymers may also be used. Examples of suitable synthetic bioabsorbable polymeric materials that can be used include poly(L-lactic acid), polycaprolactone, poly(lactide-co-glycolide), poly(ethylene-vinyl acetate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) such as PEO/PLA, polyalkylene oxalates, and polyphosphazenes. According to another exemplary embodiment of the present invention, the polymeric materials can be natural bioabsorbable polymers such as, but not limited to, fibrin, fibrinogen, cellulose, starch, collagen, and hyaluronic acid. Of course, combinations of polymers may also be employed.

In various embodiments, the polymeric compositions are configured to be implanted in a patient. The composition itself may be implanted in a patient or the composition may be included in the formation of an implantable medical device. For example, the polymeric composition may be included in a catheter or lead body, may be coated on a surface of an implantable medical device, may be disposed about a device in the form of a boot, sleeve, sheath, pouch, covering or the like.

Referring now to FIG. 1, an implantable medical device 1 having a coating 10 containing the polymer composition disposed on a surface of the device is depicted. For the purposes of FIG. 1, "coating" is used generally to include coated on a surface of the device 1 or disposed on or about the device 1 in the form of a boot, sleeve, sheath, pouch, covering or the like. The device 1 may be any implantable medical device, such as a medical lead, catheter, stent, cochlear devices, monitoring or sensing device, infusion devices, electrical signal generators, or the like. Examples of implantable electrical signal generators include cardiac pacemakers, cardioverter/defibrillators, spinal, deep brain, nerve, muscle, and gastric stimulators, and the like.

The polymeric material, with or without a compound of Formula I, may be extruded, molded, coated on a device 1. Polymers of coating 10 may be porous or non-porous. Porous materials known in the art include those disclosed in U.S. Pat. No. 5,609,629 (Fearnot et al.) and U.S. Pat. No. 5,591,227 (Dinh et al.). Typically polymers are non-porous. However, non-porous polymers may be made porous through known or developed techniques, such as extruding with $CO_2$, by foaming the polymeric material prior to extrusion or coating, or introducing and then removing a pyrogen.

Depending upon the type of materials used to form coating 10, the coating 10 can be applied to a surface of the device 1 or a coating layer (not shown) on device 1 (hereinafter referred to as "underlying coating layer") through any coating processes known or developed in the art. One method includes directly bonding the coating material to a surface of device 1 or an underlying coating layer. By directly attaching a polymer coating to device 1 or underlying coating layer, covalent chemical bonding techniques may be utilized. Surface of device 1 or underlying coating layer may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, sintering, physical vapor deposition, chemical vapor deposition, plasma enhanced chemical vapor deposition (PECVD), and etching with strong organic solvents or gas plasmas. Alternatively, coating 10 may be indirectly bound to device 1 or underlying coating layer through intermolecular attractions such as ionic or Van der Waals forces. Of course, if coating 10 is in the form of a jacket, sheath, sleeve, cover, or the like the chemical interaction between coating layer 10 and device 10 may be minimal.

A compound according to Formula I may be incorporated into a coating 10 in a variety of ways. For example, a compound according to Formula I can be covalently grafted to a polymer of the coating 10, either alone or with a surface graft polymer. Alternatively, a compound according to Formula I may be coated onto the surface of the polymer either alone or intermixed with an overcoating polymer. A compound according to Formula I may be physically blended with a polymer of a coating 10 as in a solid-solid solution. A compound according to Formula I may be impregnated into a polymer by swelling the polymer in a solution of the appropriate solvent. Any means of incorporating a compound according to Formula I into or on a coating 10 may be used, provided that a compound according to Formula I may be released, leached, diffuse from coating 10 or otherwise come into contact with bodily fluid or tissue.

A polymer of a coating 10 and a compound according to Formula I may be intimately mixed either by blending or using a solvent in which they are both soluble. This mixture can then be formed into the desired shape or coated onto an underlying structure of the medical device 1. One exemplary method includes adding one or more compound according to Formula I to a solvated polymer to form a compound according to Formula I/polymer solution. The compound according to Formula I/polymer solution can then be applied directly to the device 1 or underlying coating layer; for example, by either spraying or dip coating device 1. As the solvent dries or evaporates, the compound according to Formula I/polymer coating is deposited on device 1. Furthermore, multiple applications can be used to ensure that the coating is generally uniform and a sufficient amount of compound according to Formula I has been applied to device 1.

Alternatively, an overcoating polymer, which may or may not be the same polymer that forms the primary polymer of the surface of the device 1 (it will be understood that in some embodiments the surface of device 1 is formed of a polymeric material and in other embodiments the surface of device 1 is from non-polymeric material, such as metallic material) or underling coating layer, and a compound according to Formula I are intimately mixed, either by blending or using a solvent in which they are both soluble, and coated onto surface of device 1 or underling coating layer. Any overcoating polymer may be used, as long as the polymer is able to bond (either chemically or physically) to the polymer of an underlying layer of device 1.

In addition, a polymer of a coating 10 may be swelled with an appropriate solvent, allowing a compound according to Formula I to impregnate the polymer.

A compound according to Formula I may also be covalently grafted onto a polymer of a coating 10. This can be done with or without a surface graft polymer. Surface grafting can be initiated by corona discharge, UV irradiation, gas plasma, ozone, and ionizing radiation. Alternatively, the ceric ion method, previously disclosed in U.S. Pat. No. 5,229,172 (Cahalan et al.), may be used to initiate surface grafting.

Regardless of the process used for incorporating a compound according to Formula I into a polymeric material, the compound should generally be present in the composition at an amount effective to inhibit microbial growth. In various embodiments, the compound is present in the composition in an amount effective to inhibit growth of one or more of *Staphylococcus aureus, Staphylococcus epidermis, Escherichia coli* when implanted in a subject. By way of example, a compound according to Formula I may be present in a polymeric composition at between about 0.001 and about 40 weight percent, between about 0.01 and about 20 weight percent, or between about 0.1 and about 10 weight percent. Of course, more than one compound of Formula I may be included in the polymeric composition.

The rate of in vivo release of a compound according to Formula I or a compound according to Formula I and QOH from a polymeric material may be controlled according to any known or future developed mechanism. For example, the hydrophobicity of the polymeric material may be varied depending on the nature of the compound of Formula I, Formula II or QOH to increase or decrease the rate of release in vivo.

In various embodiments, a compound capable of hydrolyzing into a silanol is bound to a surface of an implantable medical device. A compound of Formula V below may be contacted with the surface of a device on which a free radical has been generated:

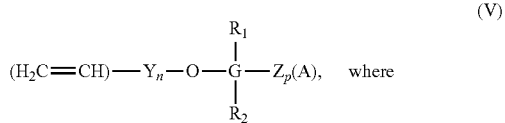

Y is straight or branched chain C1-C18 alkyl unsubstituted or substituted with halo or hydroxyl;
$R_1$ and $R_2$ are each independently hydrogen or C1-C5 straight or branched chain alkyl;
A is hydrogen or straight or branched chain C1-C18 alkyl unsubstituted or substituted with halo or hydroxyl;
Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;
G is Si or C; and
n, and p are each independently 0 or 1.

A compound according to Formula V may be made according to the following reaction scheme:

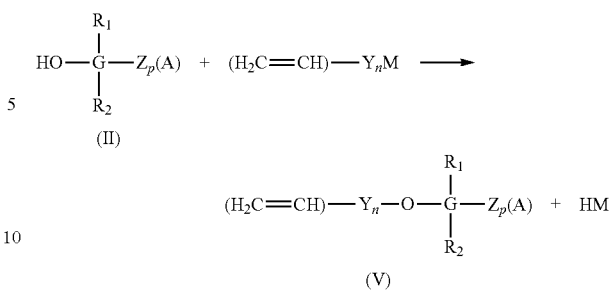

The general discussion above with regard to synthesis of compounds according to Formula I above will be similar for producing compounds of Formula V according to the reaction scheme above or otherwise, with variations reflecting differences in raw materials. Some vinyl compounds having a structure suitable for covalent bonding are allylalcohol, allyl amine, ally amide, vinyl benzoic acid, vinyl aniline, chlorostyrene, 4-vinylbenzyl chloride, etc., many of which are readily available from commercial suppliers, such as Sigma-Aldrich, Fisher and VWR.

A compound according to Formula V may be bound to a surface of an implantable medical device by contacting the compound to a surface of the device on which a free radical has been generated. Any suitable method may be employed to generate a free radical. For example, the surface can be plasma, UV or coronal treated to generate a free radical. The free radical can then react with the double bond of the vinyl group of the compound according to Formula V to bind the compound to the surface of the device.

Once implanted in a subject, the bound compound may be cleaved by hydrolysis resulting in a hydroxyl-containing compound according to Formula II, such as a silanol according to Formula IIa.

As various compounds described herein may be sensitive to hydrolysis, care should be taken during the manufacture of polymer compositions and medical devices including such compounds to minimize the exposure of such polymer compounds and devices to water. In addition, such compositions and devices are preferably stored in conditions that minimize exposure to water prior to implantation. For example, the compositions and devices may be stored or packaged with a desiccant.

One example of a useful compound according to the teachings presented herein is a compound according to Formula VI below:

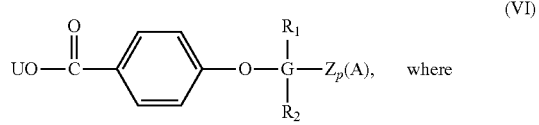

U is straight or branched chain C1-C18 alkyl unsubstituted or substituted with halo or hydroxyl;
$R_1$ and $R_2$ are each independently hydrogen, methyl, ethyl, propyl, isopropyl, or butyl;
A is hydrogen or straight or branched chain C1-C18 alkyl unsubstituted or substituted with halo or hydroxyl;
Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;

G is Si or C; and with the proviso that when p is 0, A is not hydrogen.

p is 0 or 1.

Any suitable reaction scheme and conditions may be employed to make a compound according to Formula VI. One example is to react a paraben, such as methyl paraben, with an appropriate carboxylic anhydride in a suitable solvent such as THF, acetonitrile, ether, or the like, with an appropriate catalyst.

In various embodiments, U is alkyl, such as methyl. When cleaved, a hydroxyl containing compound according to Formula II, such as a silanol according to Formula IIa, and methyl paraben, which possesses antimicrobial activity, may be released. Accordingly, added antimicrobial efficacy, relative to the silanol alone or methyl paraben alone, may be achieved.

Another example of a useful compound according to the teachings presented herein is a compound according to Formula I, where Q is a precursor to a steroid such that when hydrolyzed to Q-OH, Q-OH acts as a steroid. As steroids contain hydroxyl groups, they are readily amenable to inclusion in a compound according to Formula I and are readily amenable to be hydrolyzed as steroids. Thus, in addition to the antimicrobial effect of the hydrolyzed silanol, the anti-inflammatory effect of the steroid may be realized.

Thus, embodiments of the ANTIMICROBIAL COMPOUNDS HAVING PROTECTIVE OR THERAPEUTIC LEAVING GROUPS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A polymeric composition comprising:
a polymeric material; and
a compound according to Formula I:

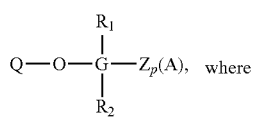

(I)

Q is a tosyl group, $R_1$ and $R_2$ are each methyl;

A is hydrogen or straight or branched chain C1-C18 alkyl unsubstituted or substituted with halo or hydroxyl;

Z is benzene, furan, pyrrole, thiophene or a cyclic structure according to Huckel's rule (4H+2), unsubstituted or substituted with straight or branched chain C1-C6 alkyl unsubstituted or substituted with halo or hydroxyl;

p is 1, and

G is silicon.

2. The composition of claim 1, wherein Q reduces volatility of the compound of formula I relative to a compound where Q is H.

3. The composition of claim 1, wherein A is hydrogen.

4. The composition of claim 1, wherein A is unsubstituted C1-C18 alkyl.

5. The composition of claim 1, wherein A is C1-C18 alkyl substituted with halo or hydroxy.

6. The composition of claim 1, wherein Z is benzene.

7. The composition of claim 1, wherein Z is furan.

8. The composition of claim 1, wherein Z is pyrrole.

9. The composition of claim 1, wherein Z is thiophene.

10. The composition of claim 1, wherein Z is a cyclic structure according to Huckel's rule (4H+2), unsubstituted or substituted with straight or branched chain C1-C6 alkyl unsubstituted or substituted with halo or hydroxyl.

11. The composition of claim 1, wherein Z is an unsubstituted cyclic structure according to Huckel's rule (4H+2).

12. The composition of claim 1, wherein Z is a cyclic structure according to Huckel's rule (4H+2), substituted with straight or branched chain C1-C6 alkyl unsubstituted or substituted with halo or hydroxyl.

13. The composition of claim 1, wherein Z is a cyclic structure according to Huckel's rule (4H+2), substituted with straight or branched chain C1-C6 alkyl unsubstituted.

14. The composition of claim 1, wherein Z is a cyclic structure according to Huckel's rule (4H+2), substituted with halo or hydroxyl.

15. The composition of claim 1, wherein A is hydrogen and Z is benzene.

16. The composition of claim 1, wherein A is hydrogen and Z is furan, pyrrole or thiophene.

17. The composition of claim 1, wherein A is unsubstituted C1-C18 alkyl and Z is benzene.

18. The composition of claim 1, wherein A is C1-C18 alkyl substituted with halo or hydroxyl and Z is benzene.

* * * * *